(12) United States Patent
Kawai

(10) Patent No.: US 7,500,393 B2
(45) Date of Patent: Mar. 10, 2009

(54) SYSTEM FOR JUDGING SKI OR SNOWBOARD

(75) Inventor: Shigehiro Kawai, Tajimi (JP)

(73) Assignee: Japana Co., Ltd., Nagoya (JP)

( * ) Notice: Subject to any disclaimer, the term of this patent is extended or adjusted under 35 U.S.C. 154(b) by 49 days.

(21) Appl. No.: 11/380,207

(22) Filed: Apr. 26, 2006

(65) Prior Publication Data
US 2006/0181074 A1 Aug. 17, 2006

(51) Int. Cl.
*A61B 5/22* (2006.01)
(52) U.S. Cl. .................... 73/379.01; 702/139
(58) Field of Classification Search ............. 73/379.01, 73/379.05, 379.08; 702/139
See application file for complete search history.

(56) References Cited

U.S. PATENT DOCUMENTS

| | | | | |
|---|---|---|---|---|
| 3,805,603 | A * | 4/1974 | Ettlinger | 73/862.02 |
| 3,988,931 | A * | 11/1976 | Perryman | 73/379.08 |
| 4,164,875 | A * | 8/1979 | Kantar et al. | 73/812 |
| 4,742,832 | A * | 5/1988 | Kauffmann et al. | 600/587 |
| 4,906,192 | A * | 3/1990 | Smithard et al. | 434/253 |
| 5,049,079 | A * | 9/1991 | Furtado et al. | 434/253 |
| 5,690,591 | A * | 11/1997 | Kenmochi et al. | 482/71 |
| 5,813,864 | A | 9/1998 | Ikuta | |
| 6,139,473 | A | 10/2000 | Koyama et al. | |
| 6,270,403 | B1 | 8/2001 | Watanabe | |
| 6,582,300 | B2 | 6/2003 | Watanabe | |
| 7,260,545 | B1 * | 8/2007 | Schaer et al. | 705/1 |
| 2003/0017883 | A1 | 1/2003 | Yoshiike | |
| 2006/0179938 | A1 * | 8/2006 | Kawai | 73/379.01 |

FOREIGN PATENT DOCUMENTS

| JP | 0190585 U | 6/1989 |
|---|---|---|
| JP | H03-212263 A | 9/1991 |
| JP | H05-33032 U | 4/1993 |
| JP | H07-213745 A | 8/1995 |
| JP | 08-131594 A | 5/1996 |
| JP | 09-149957 A | 6/1997 |
| JP | H09-224922 A | 9/1997 |
| JP | 10-085453 A | 4/1998 |
| JP | 11-156047 A | 6/1999 |
| JP | 2002-048630 A | 2/2002 |

(Continued)

OTHER PUBLICATIONS

PCT Written Opinion of International Searching Authority for International Application Serial No. PCT/JP2005/001898.

*Primary Examiner*—Harshad Patel
*Assistant Examiner*—Punam Patel
(74) *Attorney, Agent, or Firm*—Hiroe & Associates; Michael L. Crapenhoft

(57) ABSTRACT

A system for judging a ski or snowboard allows a ski board or snowboard most suitable for each skier or snowboarder to be judged by considering the leg strength of each skier or snowboarder. The system includes a storage means for storing a bending characteristic of the ski or snowboard, an input means for inputting the weight and leg strength of the skier or snowboarder, a board characteristic detecting means for determining a bending characteristic of a ski or snowboard that corresponds to the weight and leg strength, and a board searching means for searching the storage means for skis or snowboards that correspond to the bending characteristics determined by the board characteristic detecting means.

8 Claims, 21 Drawing Sheets

FOREIGN PATENT DOCUMENTS

| | | |
|---|---|---|
| JP | 2002-065652 A | 3/2002 |
| JP | 2002-136632 A | 5/2002 |
| JP | 2002-312371 A | 10/2002 |
| JP | 2002-346015 A | 12/2002 |
| JP | 2003-199728 A | 7/2003 |
| JP | 2003-240630 A | 8/2003 |
| WO | WO98/10847 | 3/1998 |

* cited by examiner

Fig.3

CUSTOMER REGISTRATION SCREEN

| YOUR NAME | LAST NAME [　　] FIRST NAME [　　] |
| PHONETIC SPELLING | LAST NAME [　　] FIRST NAME [　　] |
| ADDRESS | [　　　　　　　　　　] — 11 |
| TEL | [　　]—[　　]—[　　] |
| FAX | [　　]—[　　]—[　　] — 11 |
| E-mail | [　　　　　　　　　　] |
| BIRTHDAY | [　]YEAR [　]MONTH [　]DAY — 11 |
| GENDER | MALE ○  FEMALE ○ |
| HEIGHT | [　　] cm |
| FOOT SIZE | [　　] cm |
| QUALIFICATION | [FIRST GRADE ▽] |
| USUAL SKIING LOCATION | [　　　　　▽] |
| USUAL NUMBER OF DAYS SKIED PER YEAR | [30 DAYS] |

CURRENT USE GOODS

| SKI SNOWBOARD | [　　　▽] | POLES | [　　　▽] |
| BOOTS | [　　　▽] | TASTE FOR COLORS | [　　　▽] |
| BINDING | [　　　▽] | | |

( RESET )    ( CONFIRM )
   13            12

7

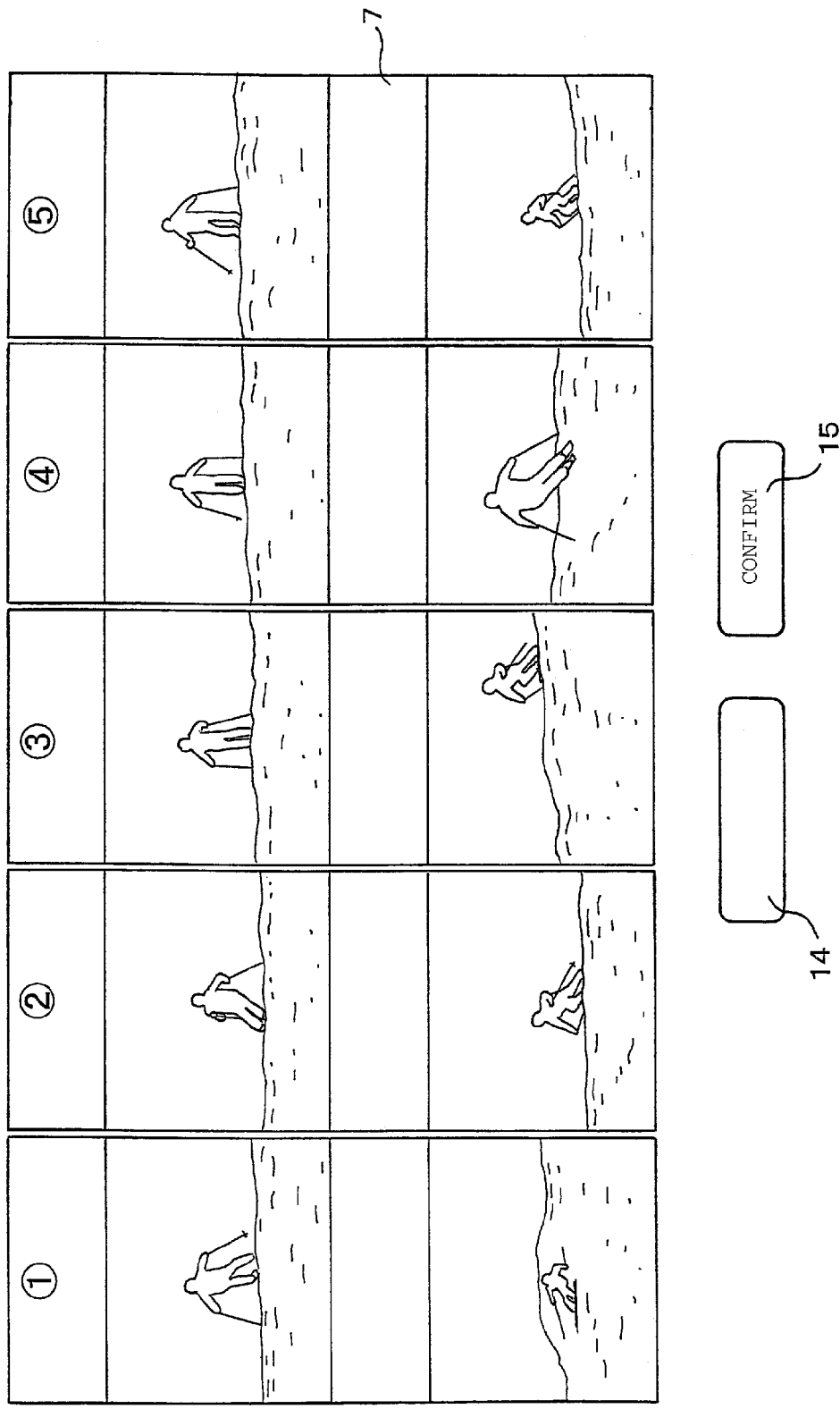

Fig.5

```
QUESTION 1:  HAVE YOU EVER PARTICITATED
             IN SKI TOURNAMENT?
                 YES ○         NO ○
QUESTION 2:  HAVE YOU EVER RECEIVED
             QULIFICATION TEST?
                 YES ○         NO ○
QUESTION 3:  ARE YOU ABLE TO MAKE
             CURVING TURNS WITHOUT DEVIATIONS
                 YES ○         NO ○
QUESTION 4:  ARE YOU SKILLFUL AT LARGE TURN?
                 YES ○         NO ○
QUESTION 5:  ARE YOU ABLE TO RUN IN BUMPY SLOPE
             WITH LARGE TURN?
                 YES ○         NO ○
QUESTION 6:  ARE YOU ABLE TO CONTROL DEVIATION?
                 YES ○         NO ○
QUESTION 7:  ARE YOU SKILLFUL AT SMALL TURN?
                 YES ○         NO ○
QUESTION 8:  ARE YOU USING CURVING SKI?
                 YES ○         NO ○
QUESTION 9:  HAVE EVER RECEIVED LESSON
             IN SKI SCHOOL
                 YES ○         NO ○
QUESTION 10: DO YOU KEEP TECHNICAL IMPROVEMENT
             IN MIND ALWAYS?
                 YES ○         NO ○
```

( RESET )         ( CONFIRM )
    17                 16

Fig.6

| WEIGHT | 75kg |
|---|---|
| LEG STRENGTH | 145kg |
| AC (WEIGHT/ LEG STRENGTH) | 1.93 |
| MAXIMUM LOAD | 220kg |
| SKILL LEVEL | AB |

SKI DATA

BEND CHARACTERISTIC [ HARD ]
TORSION CHARACTERISTIC [ MIDDLE ]

○ LARGE TURN GROUP   ○ MIDDLE TURN GROUP   ● SMALL TURN GROUP

| No | BRAND | PRODUCT NAME | SIZE | FLEX | TORSION | COMMENTS | DETAILS |
|---|---|---|---|---|---|---|---|
| 1 | ○○○○ | △△△△ | 150 | HARD | MIDDLE | THIS BOARD······ | △ 18 |
| 2 | ○×○× | △○△○ | 165 | HARD | MIDDLE | THIS BOARD······ | △ 18 |
| 3 | □□□□ | ××○○ | 160 | HARD | MIDDLE | THIS BOARD······ | △ 18 |
| 4 | ○○□○ | △×△× | 158 | HARD | MIDDLE | THIS BOARD······ | △ 18 |
| 5 | | | | | | | |
| 6 | | | | | | | |

Fig.7

| BENDING CHARACTERISTIC | MAXIMUM LOAD | | |
|---|---|---|---|
| | EQUAL TO OR LARGER THAN 200 kgf | 200 kgf to 100 kgf | EQUAL TO OR SMALLER THAN 100 kgf |
| | HARD | MIDDLE | SOFT |

SYSTEM FOR JUDGING SKI OR SNOWBOARD

BACKGROUND OF THE INVENTION

The present invention relates to sporting goods, and in particular to skis and snowboards. More specifically, the invention provides a system for judging and selecting a ski or snowboard that, based upon the weight and leg strength of a skier or snowboarder, allows for the assessment and selection of a ski or snowboard suitable for that particular user.

Skis and snowboards suitable for each skier or snowboarder are preferably judged and selected based on the weight and leg strength of that individual skier or snowboarder.

A customer goes to a shop and selects a favorite ski or snowboard when purchasing the ski or snowboard.

Customers have generally selected skis and snowboards based upon their own height or physical figure, depending mainly on intuition, and without relying upon definite criteria, whereby there have been many cases where the customer purchases a ski or snowboard, that a clerk of a sales shop perhaps recommends, and without any doubt thereabout, but selected mainly based simply on price or appearance, so it has been difficult to accurately purchase skis or snowboards suitable for the physical characteristics of each individual skier or snowboarder including the leg strength of that particular user.

Japanese Laid-open Patent Application No. 2002-312371 describes a method for searching for a ski or snowboard suitable for each skier or snowboarder by determining the size and flex of each part of the ski or snowboard as suitable for each skier or snowboarder from physical information such as the age, weight, and height of each skier or snowboarder.

However, the above-mentioned conventional method for searching for sporting goods, which is by judging the ski or snowboard suitable for the skier or snowboarder from physical characteristics such as the age, the weight, and the height of each skier or snowboarder, is not a method for judging the ski or snowboard suitable for each skier or snowboarder with consideration given to the user's leg strength, which is the most important element in judging the ski or snowboard suitable for each skier or snowboarder. For this reason, it has been difficult to judge and select a ski or snowboard most suitable for each skier or snowboarder.

Accordingly, there has been a problem that re-investigation is required by each skier or snowboarder as to whether or not the searched for and selected ski or snowboard is suitable for the user's own leg strength.

The present invention has been made in consideration of the actualities of the foregoing prior art, with an eye toward providing a system for judging a ski or snowboard that allows the ski board or snowboard most suitable for each skier or snowboarder to be selected with consideration given to the leg strength of each skier or snowboarder.

The invention may also provide a system for judging a ski or snowboard that can be utilized for the development and a design of skis or snowboards suitable for various individual users.

SUMMARY OF THE INVENTION

One embodiment of the invention includes a storage means for storing bend characteristics of a plurality of types of skis or snowboards, an input means for inputting the weight and leg strength of a skier or snowboarder, a board characteristic detecting means for determining bend characteristics of the ski corresponding to the weight and leg strength, and a board searching means for searching the storage means for skis or snowboards corresponding to the bend characteristic determined by the board characteristic detecting means.

Such an embodiment allows for the assessment and selection of a ski or snowboard that is suitable for an individual skier or snowboarder based upon his weight and leg strength.

Some embodiments will include a storage means for storing information corresponding to skis or snowboards suitable for a level of skiing or snowboarding skill or technique, an input means for inputting the level of skill or technique, a board characteristic detecting means for determining torsion characteristics of skis or snowboards corresponding to the user's skill level, and a board searching means for searching the storage means for skis or snowboards that correspond to the torsion characteristics determined by the board characteristic detecting means.

This enables the selection and assessment of skis or snowboards suitable for the skier or snowboarder based upon his level of skill or technique.

Some embodiments will include storage means in which skis or snowboards suitable for particular styles of use are stored, input means into which a usage style suiting the preference of the skier or snowboarder is input, and a board searching means for searching the storage means for skis or snowboards suitable for the style of use that suits the taste of the skier or snowboarder input from the input means.

Such a system enables a ski or snowboard suitable for style of use that suits the taste of the skier or snowboarder to be judged and selected.

Some embodiments will include storage means in which information corresponding to skis or snowboards suitable for the height, body type, and the age of the skier or snowboarder are stored, an input means into which the height, the body type, and the age of the skier or snowboarder are input, and a board searching means for searching for the ski or snowboard suitable for the height, body type, and the age of the skier or snowboarder input from the input means.

Such a system enables the assessment and selection of skis or snowboards suitable for the height, body type, and the age of the skier or snowboarder.

Some embodiments will include a leg strength measuring apparatus for measuring a user's leg strength.

These embodiments enable the leg strength of the skier or snowboarder to be measured automatically.

In some embodiments the leg strength measuring apparatus includes two footplates, onto which a person whose leg strength is to be measured steps separately with his left and right feet, and a load sensor for detecting loads applied to each footplate at three or more spaced-apart points.

Such a system enables the measurement of planar distributions of loads applied by the feet of a person whose leg strength is measured.

In some embodiments the leg strength measuring apparatus includes two footplates, onto which a person whose leg strength is to be measured steps separately with his left and right feet, and a load sensor for detecting a vertical load applied to each footplate and a moment about each of the footplates.

Such a system will enable the determination of the weight of the person and the state of the planar distribution of loads when making bending and stretching motions at the knees with only one load sensor in each footplate.

Some embodiments include leg strength measuring apparatus with leg strength calculation means for calculating the leg strength of the person by subtracting the weight of the person from a maximum load that is detected by the load sensor while the person is standing on the footplates and making bending and stretching motions.

Such systems allow the leg strength of the person to be calculated by subtracting the person's weight from the maximum load that is measured when the person makes bending and stretching motions while standing on the footplates.

Some embodiments include storage means for storing the maximum load and weight of the person based upon an output from a load sensor.

Such an embodiment enables the maximum load and the leg strength to be obtained as the person bends and stretches, based upon the measured values stored in the storage means.

Some embodiments may include a gap adjustment means for adjusting a separation gap between two footplates.

Such embodiments allow the separation gap between the two footplates to be adjusted as appropriate for each user.

Some embodiments may include a handrail.

Such embodiments help to ensure the safety of the person stepping onto the system.

In some embodiments the handrail moves together with one of the footplates.

This allows a person to stand on the footplate while grasping the handrail.

Some embodiments may include footplates with a boot fixing section for fixing skis or snowboard boots in place on the system.

This enables a person to stand on the footplates while wearing ski or snowboard shoes.

Some embodiments include a load sensor that is capable of detecting a plurality of momentary values during a user's bending and stretching movements.

Such embodiments enable the detection of conditions corresponding to the user's weight shifts in the course of his bending and stretching movements.

Some embodiments include an analyzing means for analyzing planar distributions of loads determined based upon output values from the system's load sensors.

Such an embodiment allows the planar load distributions to be analyzed.

Some embodiments have footplates with a shape that allows the ski or snowboard to be mounted readily thereon.

This allows a user to stand and move on the footplates while wearing the skis or the snowboard.

Preferred embodiments will include footplates that are formed as rigid members that resist deformation.

This enables the efficient transmission of loads applied to the footplate to the load sensor because the footplate is difficult to deform.

Some embodiments may allow footplates to be fixed in an inclined state in directions from front-to-back or side-to-side.

Such embodiments make it possible to measure the leg strength while inclining the footplates in positions that reflect situations in which the person is actually skiing or snowboarding.

Some embodiments are capable of generating a simulation display of a ski or snowboard run using the ski or snowboard judged to be suitable for each skier or snowboarder.

This allows each skier or snowboarder to visually confirm whether or not the ski or snowboard in question is a suitable one, based on the simulation display.

DESCRIPTION OF THE FIGURES

The following detailed description of preferred embodiments of the invention will be better understood with reference to the appended drawings, in which:

FIG. 3 is display contents of a display;

FIG. 4 is further display contents of the display;

FIG. 5 is further display contents of the display;

FIG. 6 is further display contents of the display;

FIG. 7 is a graph illustrating a relation between a maximum load and a bending characteristic for a ski or a snowboard;

DESCRIPTION OF PREFERRED EMBODIMENTS

Figure 1:
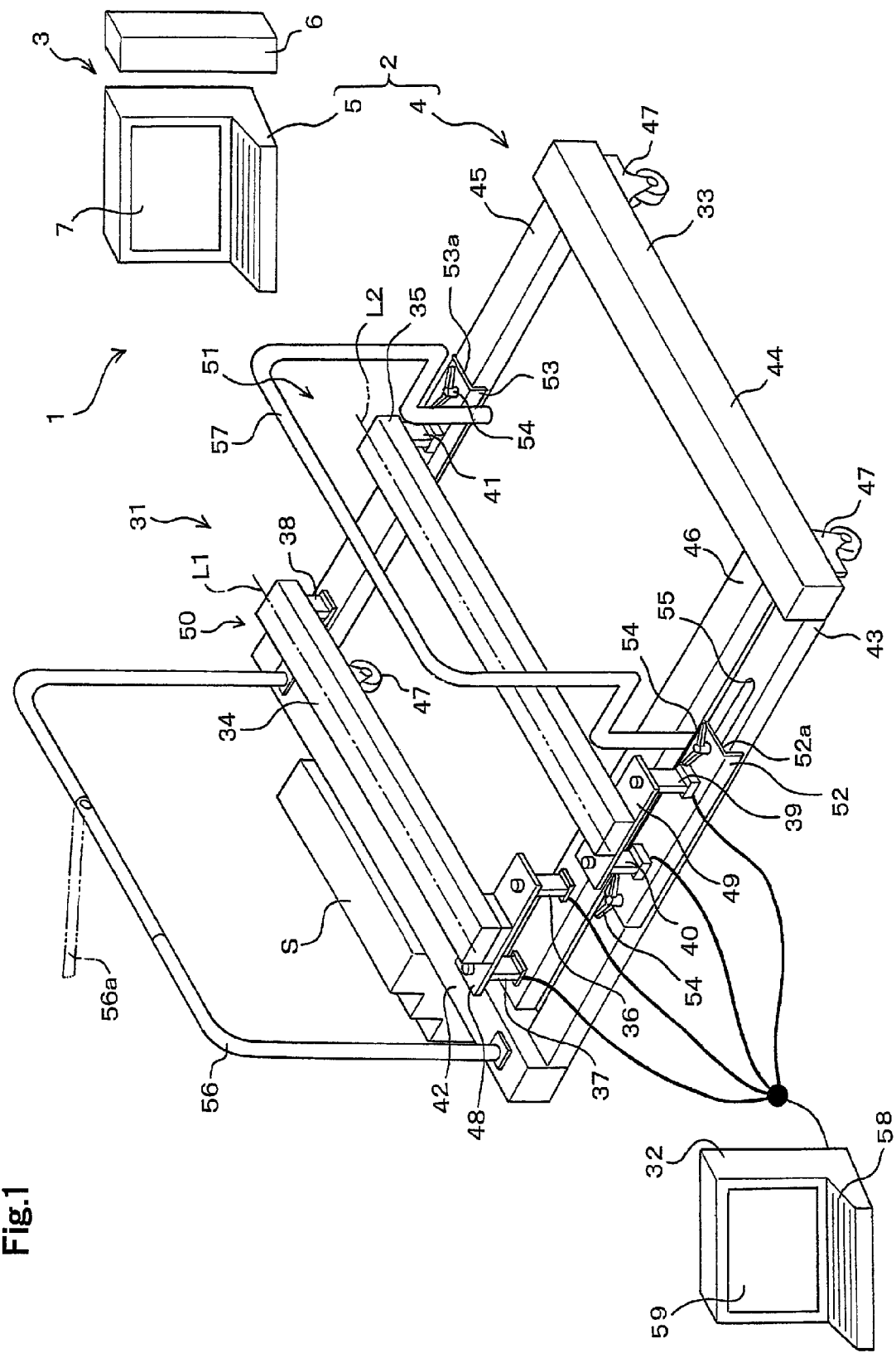
FIG. 1 is a system for judging and selecting a ski or snowboard.

FIG. 1 illustrates a system 1 for judging or selecting a ski or snowboard. The system 1 includes an input means 2 for inputting information corresponding to an individual skier or snowboarder, and a personal computer (hereinafter, referred to as a PC) 3 for, based upon the information for the skier or snowboarder input from the input means 2, searching for a ski or snowboard suitable for the skier or snowboarder.

The weight and leg strength of the skier or snowboarder, the type and usage of the ski or snowboard, etc. are listed as information for the skier or snowboarder.

A weight and leg strength measuring apparatus 4, a keyboard 5, etc. are listed as the input means 2. The PC 3 includes a PC body 6, a display 7 as a peripheral appliance for the PC body 6, and a keyboard 5 as the input means 2.

Figure 2:
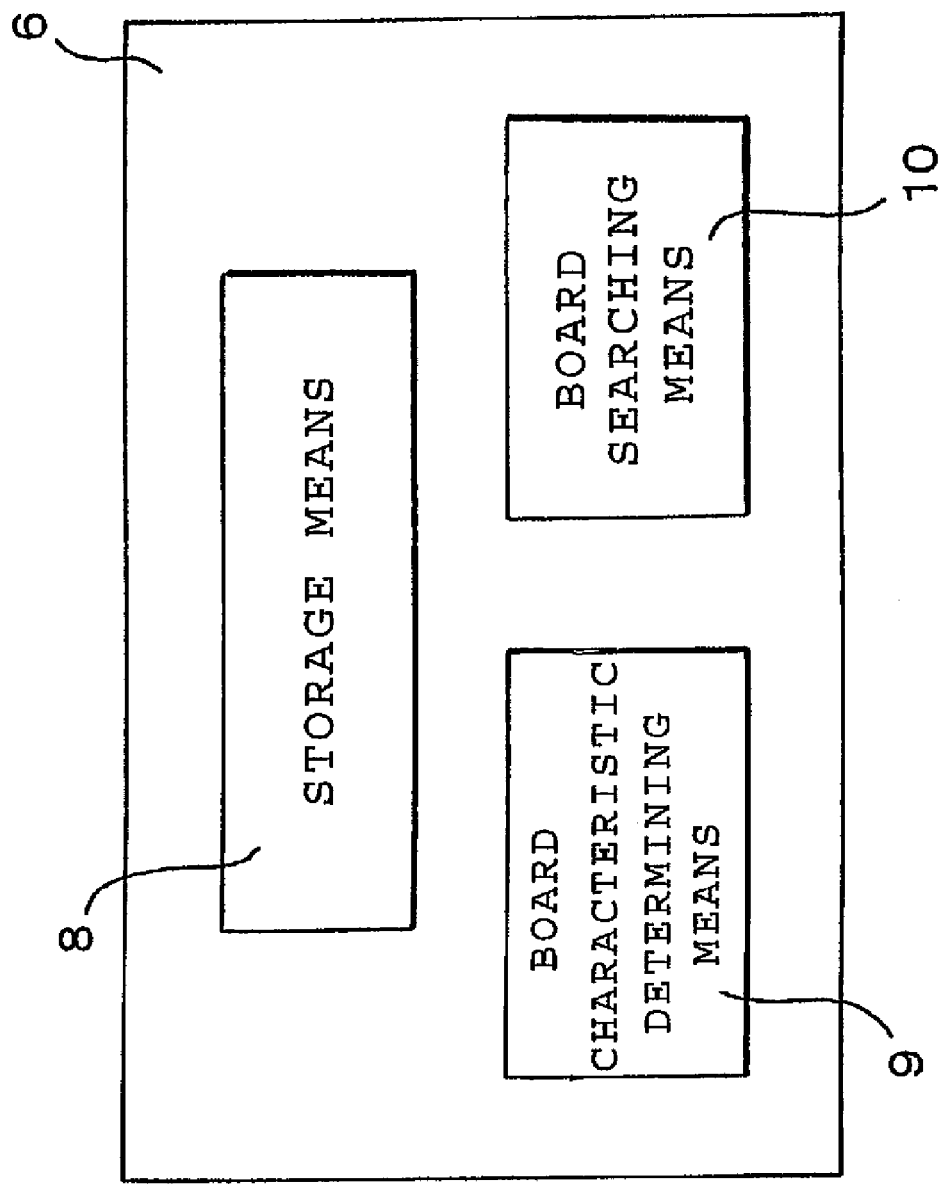
FIG. 2 is a block diagram.

The weight and leg strength of the skier or snowboarder are measured in the weight and leg strength measuring apparatus 4 and input into the PC 3. Furthermore, the skill level, technique, or usage style of the skier or snowboarder is key-input through the keyboard 5. The method will be described later of inputting the weight and leg strength of the skier or snowboarder, and the skill level, technique, or usage style. As shown in FIG. 2, the PC body 6 of the PC 3 includes a CPU (not shown), a ROM (not shown) and a RAM as the storage means 8. The skis or snowboards are divided into groups and stored in the storage means 8, depending upon the magnitudes of the bend and torsion characteristic of the skis or snowboards.

Predetermined program software is embedded in the ROM in advance. The CPU reads out the program software, thereby allowing board characteristic detecting means 9 and board searching means 10 to be deployed as shown in FIG. 2.

The board characteristic detecting means 9 is capable of determining the bending characteristics of the ski or snowboard based on the weight and leg strength of the skier or snowboarder. That is, a large load is applied to the ski or snowboard as a skier or snowboarder bears heavily or exerts a strong leg force on the ski or snowboard. The board characteristic detecting means 9 determines that a greater bending resistance is required as a characteristic of the ski or snowboard as the weight and leg strength of the skier or snowboarder increase, so that the ski or snowboard is capable of bearing the greater load.

Furthermore, the board characteristic detecting means 9 is capable of determining torsion characteristics of the ski or snowboard by the technique or skill exercised by the user in skiing or snowboarding. That is, a skier or snowboarder has a tendency of using the ski or snowboard by raising its edges, a tendency which generally increases as the user's skill becomes greater, and in the case of making such a run, a large torsion is applied to the ski or snowboard. For this, the board characteristic detecting means 9 considers that a ski or snowboard having a strong resistance against torsion is suitable for the skier or snowboarder having a high level of skill or advanced technique.

The board searching means 10 is for selecting a ski or snowboard having the characteristics determined in the board characteristic determining means 9 by searching the storage means 8 for appropriate items stored therein.

Furthermore, predetermined program software is embedded in the ROM of the PC 3, and operations of the keyboard 5, the display 7, and the storage means 8 are controlled based upon this program software.

Next, the method will be described of inputting factors relating to the technique of the skier or snowboarder through the keyboard 5 and the display 7.

The keyboard 5 and the display 7 are employed together, with an operator operating the keyboard while responding to information displayed on the display 7. The operator enters information corresponding to the skill level of the skier or snowboarder by inputting predetermined items by means of the keyboard. With a customer registration screen as shown in FIG. 3 displayed in the display 7, predetermined items used to specify and identify the customer are key-input into blanks 11 on the customer registration screen. As FIG. 3 illustrates, a confirmation icon 12 is clicked to confirm the information entered on the display. Clicking a reset icon 13, on the other hand, resets the screen so that new information can be entered. Furthermore, when an art level image screen as shown in FIG. 4 is displayed in the display 7, the number of the display image within the art level image screen that corresponds to the customers own ski technique is input into a blank 14. Then, a confirmation icon 15 can be clicked to confirm the input item. The information items input from the keyboard 5 are stored in the storage means 8 (shown in FIG. 2) of the PC 3.

Next, an answer is selected by clicking [Yes] or [No] for each of the inquiries illustrated in FIG. 5, for example [Question 1: Have you participated in a skiing tournament?], [Question 2: Have you received a qualifying test?], etc. When all of the questions have been answered, clicking a confirmation icon 16 confirms the entries. Clicking a reset icon 17, on the other hand, resets all of the entries so that the questions can be answered again.

As described above, the number of the display image corresponding to the user's skill level or technique is selected from the skill level image screen shown in FIG. 4 and input into the blank 14. By responding to each inquiry shown in FIG. 5, moreover, the skill level of the skier or snowboarder is determined and input.

FIG. 6 illustrates a display of the weight and leg strength of a skier or snowboarder. The display also shows the maximum load obtained by adding the weight and the leg strength, the bending characteristic of the ski or snowboard responding to the weight, leg strength and maximum load, the skill level of the skier or snowboarder, and the torsion characteristic of the ski or snowboard that corresponds to the skier or snowboarder's technique. Information identifying several skis or snowboards that correspond to the bending and torsion characteristics determined in such a manner is also displayed. FIG. 6 shows a case where the user's weight is 75 kgf, the user's leg strength is 145 kgf, the maximum load (by addition of the weight and leg strength) is 220 kgf, and the bending characteristic is HARD. In FIG. 6, moreover, the user's skill level is specified as "AB", and the torsion characteristic for the ski is MIDDLE. Four skis or snowboards are displayed. These items have a bending characteristic of HARD and a torsion characteristic of MIDDLE. As shown in FIG. 7, the bending characteristic can classified as HARD, MIDDLE, or SOFT based upon the numerical value of the maximum load; however, the range of numerical values described in FIG. 7 can be changed arbitrarily. As is described previously, the weight, leg strength and maximum load obtained by adding the weight and leg strength are measured by the leg strength measuring apparatus 4 (shown in FIG. 1), which is described in more detail below. The bending characteristic of the ski or snowboard is determined by the board characteristic determining means 9. The skill level and technique of the skier or snowboarder is key-input with the keyboard 5. The torsion characteristic of the ski or snowboard is determined by the board characteristic determining means 9 based upon the skill and technique of the skier or snowboarder.

Figure 8:
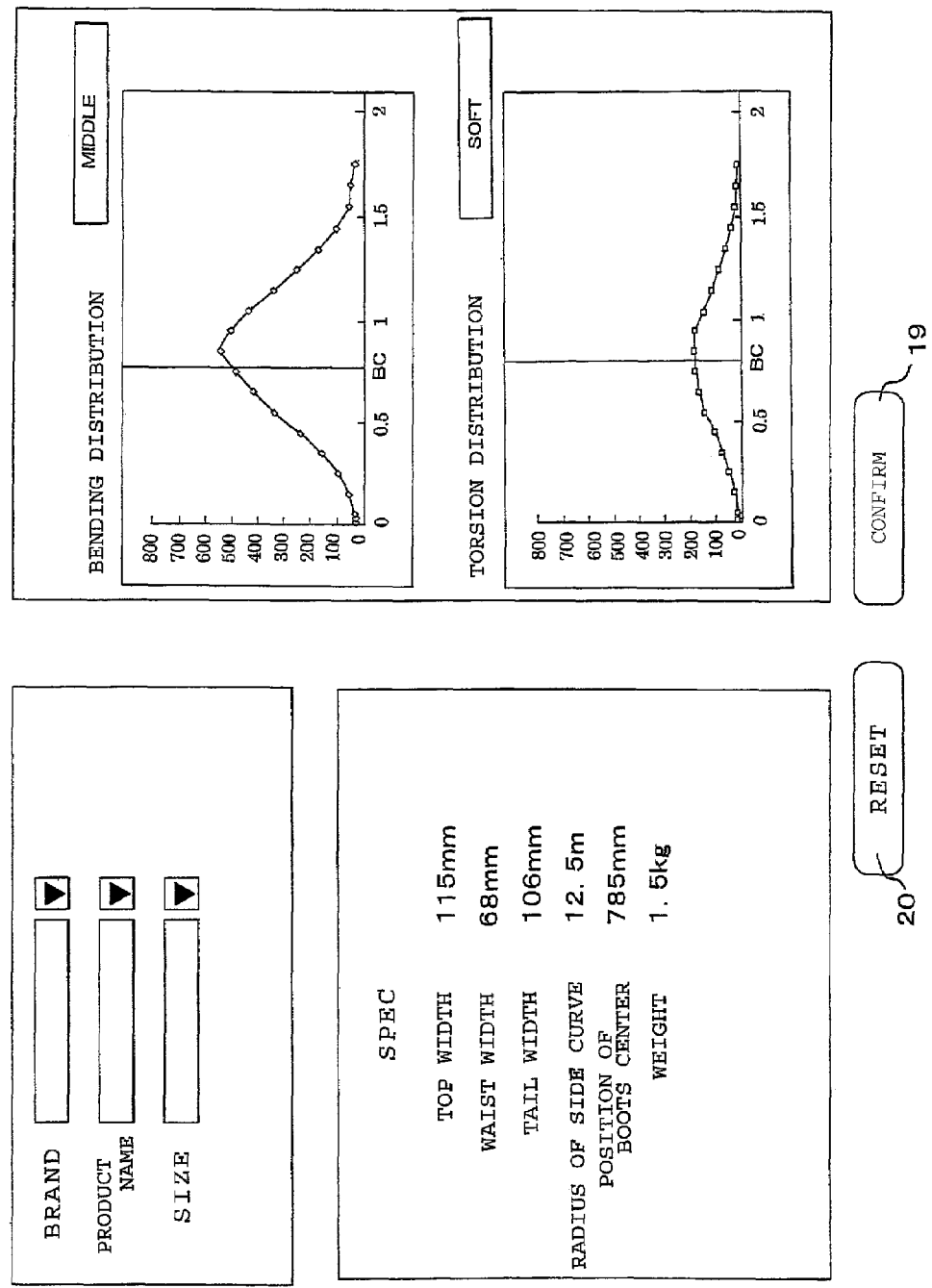
FIG. 8 is further display contents of the display.
Figure 9:
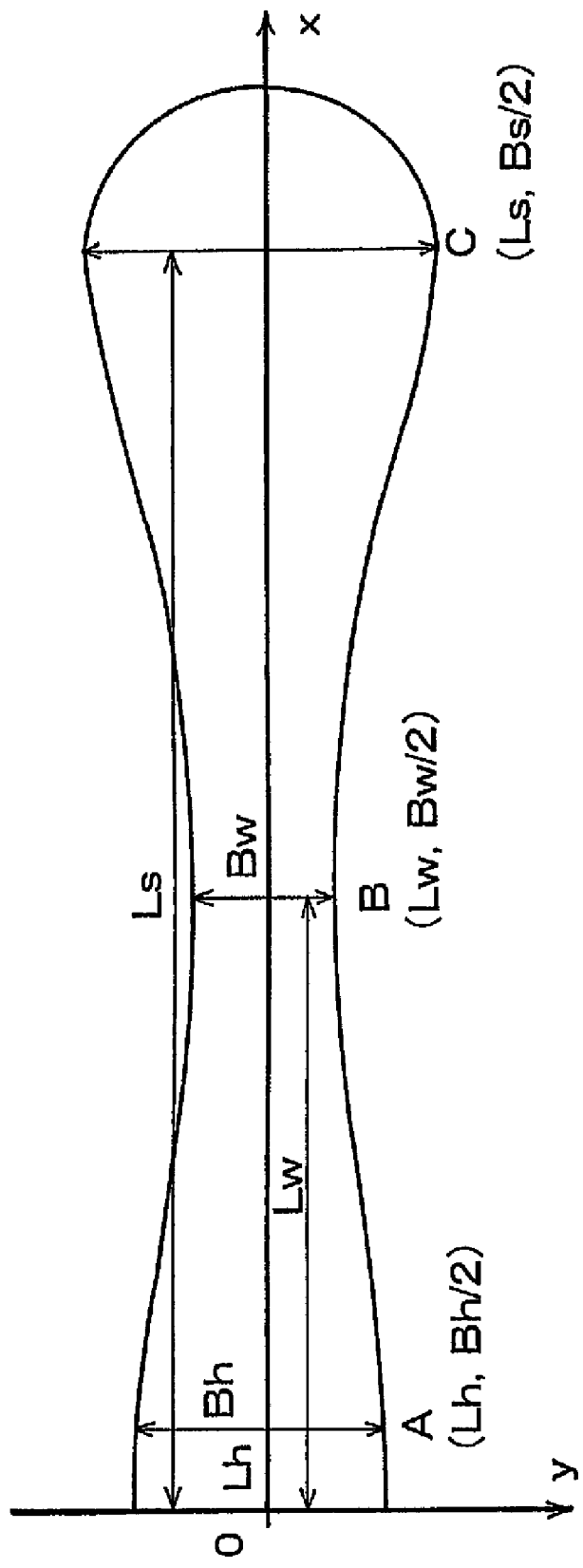
FIG. 9 is a view illustrating a coordinate system for a ski.
Figure 10:
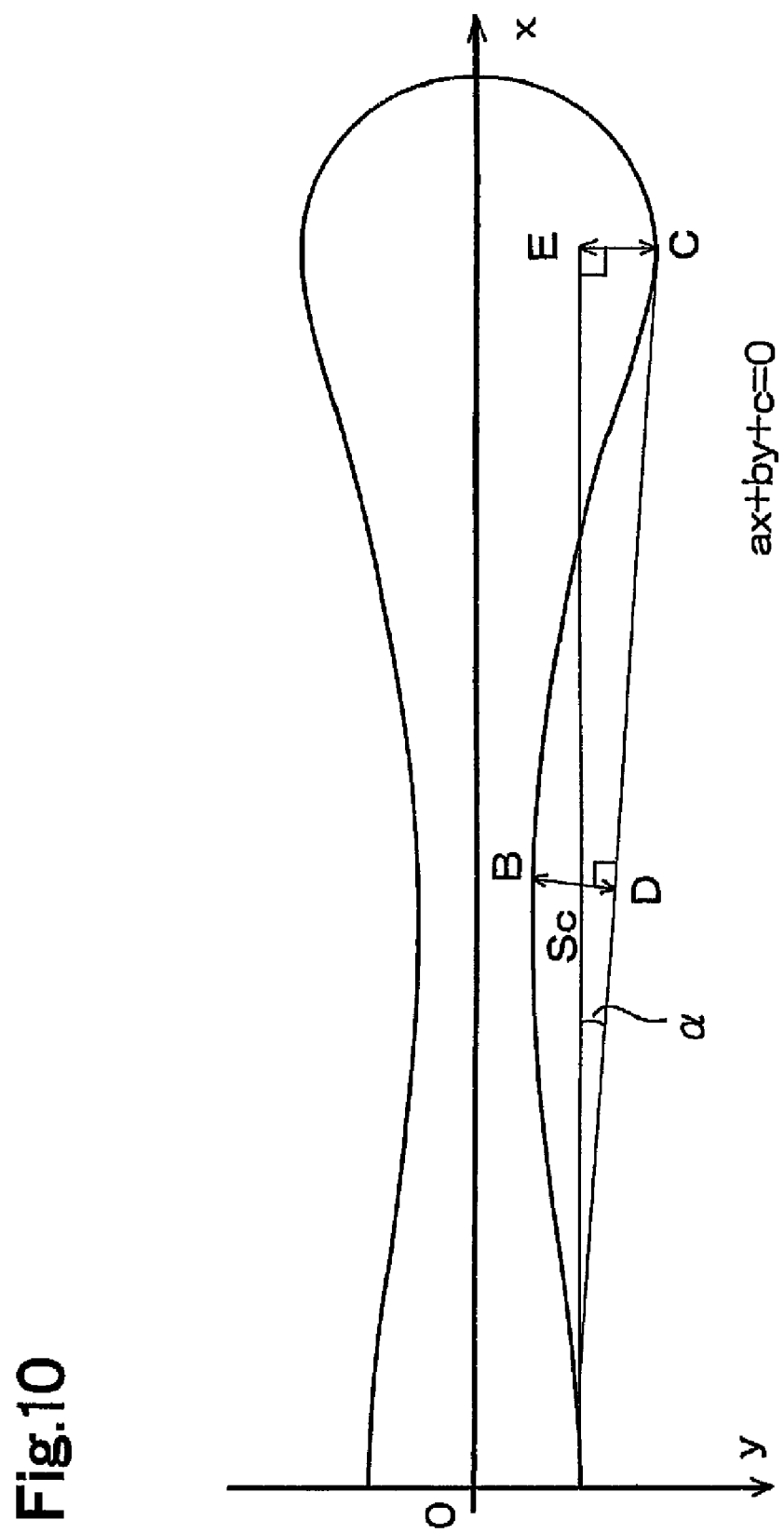
FIG. 10 illustrates an analysis of a turn arc for the ski.

Clicking a detail display icon 18 illustrated in FIG. 6 will display details of each of the relevant skis or snowboards. FIG. 7 shows a state in which a No. 1 ski or snowboard is selected in FIG. 6, and its details are displayed. FIG. 8 shows as the details of the ski and snowboard a brand, an item name and size, and additionally, a top width, a waist width, a tail width, a side curve radius, a boot center position, the weight of the ski or snowboard, and the bending and torsion distributions of the ski or snowboard. A shoulder width Bs, a waist width Bw, a tail width Bh, and a boot center position B are illustrated in FIG. 9.

Clicking a confirmation icon 19 shown in FIG. 8, selects for the customer the ski or snowboard for which the details are displayed as shown in FIG. 8. Clicking a reset icon 20, on the other hand, rejects the ski or snowboard for which the details are displayed as shown in FIG. 8. The specific arrangement of the weight/leg strength measuring apparatus 4 shown in FIG. 1, and the methods for inputting the weight and leg strength of the skier or snowboarder by this weight/leg strength measuring apparatus 4 will be described in more detail below.

The leg strength measuring apparatus 4 shown in FIG. 1 includes a measurer 31, and a personal computer (hereinafter, referred to as a PC) 32. The measurer 31 is an appliance for measuring a load such as the weight of the person to be measured. The PC 32 is used to input the values measured by the measurer 31 and to execute a process for calculating the leg strength of the person, the planar distribution of the applied loads, etc. The measurer 31 includes a base stand 33, with two footplates 34 and 35 provided on the base stand 33 in parallel to each other. The footplates 34 and 35 are spaced apart so that the person whose leg strength is measured can step on them individually with his left and right feet. Three load sensors 36, 37, and 38 are located between one footplate 34 and the base stand 33. Three other load sensors 39, 40, and 41 are located between the other footplate 35 and the base stand 33. The sensors 36 to 41 are used to detect the loads applied to the footplates 34 and 35.

The base stand 33 may be formed in any desirable shape suitable for supporting the footplates 34 and 35. It may, as one example, be formed as a four-cornered framework with four supporting bodies 42, 43, 44 and 45 assembled in a square. It may also be formed with an auxiliary body 46 assembled in parallel to the supporting body 43. Providing casters 47 at the four corners of the base stand 33 allows the base stand 33 to be made movable and positioned as desired. A base stand 33 having such a configuration allows one footplate 34 to be constructed as a span between the supporting body 45 and the auxiliary body 46, with the other footplate 35 constructed as a span between the supporting body 43 and the supporting body 45.

The footplates 34 and 35 may be long and narrow. Both footplates 34 and 35 are preferably formed of a rigid member that is not susceptible to deformations such as bending and deflection, so that the loads applied to the footplates 34 and 35 are efficiently transmitted to the load sensors 36 to 41. A sensor fitting section 48 that is wider than the footplate 34 is fixed to the back side of a tip in of one footplate 34. The load censors 36 and 37 are provided at the back side of the sensor fitting section 48. Furthermore, the load censor 38 is provided at the back side of the rear end of the footplate 34.

A sensor fitting section 49 that is wider than the footplate 35 is fixed to the back side of a tip at one end of the other footplate 35. Load censors 39 and 40 are provided on the back side of the sensor fitting section 49, and a load sensor 41 is provided at the back side of the rear end of the footplate 35. The assembly comprising sensor fitting section 48 and the three load sensors 36 to 38 for one footplate 34 makes up one footplate unit 50, with the assembly comprising the sensor fitting section 49 and the three load sensors 39 to 41 for the other footplate 35 making up a second footplate unit 51. As FIG. 1 illustrates, the load sensor 38 is positioned on an axial line L1 of one footplate 34, with the load sensors 36 and 37 placed at positions that form an isosceles triangle together with the load censor 38. The load sensor 41 is positioned on an axial line L2 of the other footplate 35, and the load sensors 39 and 40 are placed at positions that form another isosceles triangle together with the load censor 41.

One footplate unit 50, whose arrangement is described above, is constructed as a span between the supporting body 45 and the auxiliary body 46. The footplate unit 50 is fixed to the auxiliary body 46 and the supporting body 45 with the two load sensors 36 and 37 of the footplate unit 50 interposed between the sensor fitting section 48 and the auxiliary body 46 and with the load sensor 38 interposed between the footplate 34 and the supporting body 45.

Because the other footplate unit 51 is constructed as a span between the supporting body 43 and the supporting body 45, it can be moved along the supporting body 43 and that supporting body 45. Fitting moving bodies 52 and 53 movably onto the supporting bodies 43 and 45 and fixing the tip and the rear end of the movable footplate unit 51 to these two moving bodies 52 and 53 enables the movable footplate unit 51 to move toward and away from the first footplate unit 50 along the longitudinal direction of the two supporting bodies 43 and 45. This arrangement makes it possible to adjust the separation gap between the two footplate units 50 and 51 as desired.

The moving bodies 52 and 53 may be formed, for example, with roughly C-shaped cross-sections as shown in FIG. 1. The moving body 52 can be fitted onto the supporting body 43 so that the open side 52a of the C-shaped cross-section fits over the supporting body 43. The moving body 53 can be fitted in a similar way onto the supporting body 45 with its open side 53a fitted over the supporting body 45. The moving bodies 52 and 53 are thus fitted onto and movable along the length of the two supporting bodies 43 and 45. The tip side of the movable footplate unit 51 is mounted on the moving body 52 with the two load sensors 39 and 40 interposed between the sensor fitting section 49 and the moving body 52. The rear end side of the footplate unit 51 is mounted on the moving body 53 with the load sensor 41 interposed between the footplate 35 and the moving body 53.

The moving bodies 52 and 53 are bored to receive screws 54 so that the moving bodies 52 and 53 can be positioned with respect to the supporting bodies 43 and 45. Elongate holes 55 are provided along the length of the supporting bodies 43 and 45. The screws 54 and nuts (not shown) can be tightened against the edges of the elongate holes 55 to fix the moving bodies in position on the supporting bodies 43 and 45.

The moving bodies 52 and 53 and the screws 54 thus comprise a gap adjustment means that allows the adjustment of the separation gap between the footplates 34 and 35.

All of the load sensors 36 to 41 provided in both of the footplate units 50 and 51 are set so that the loads applied to the footplates 34 and 35 are measured at the same sampling interval.

A handrail 56 is fixed to the supporting body 42. The two ends of another handrail 57 are fixed to the moving bodies 43 and 45, which allows the other handrail 57 to move together with the movable footplate unit 51 and the moving bodies 52 and 53. Providing a grip made of rubber, etc. on both of the handrails 56 and 57 allows easy gripping. Furthermore, as shown by a broken line in FIG. 1, an opener/closer 56a can be provided in one portion of the handrail 56 on the fixture side to allow a person to pass through the handrail. A step S may also be provided to enable the person to easily step onto the footplates 34 and 35.

Figure 12:
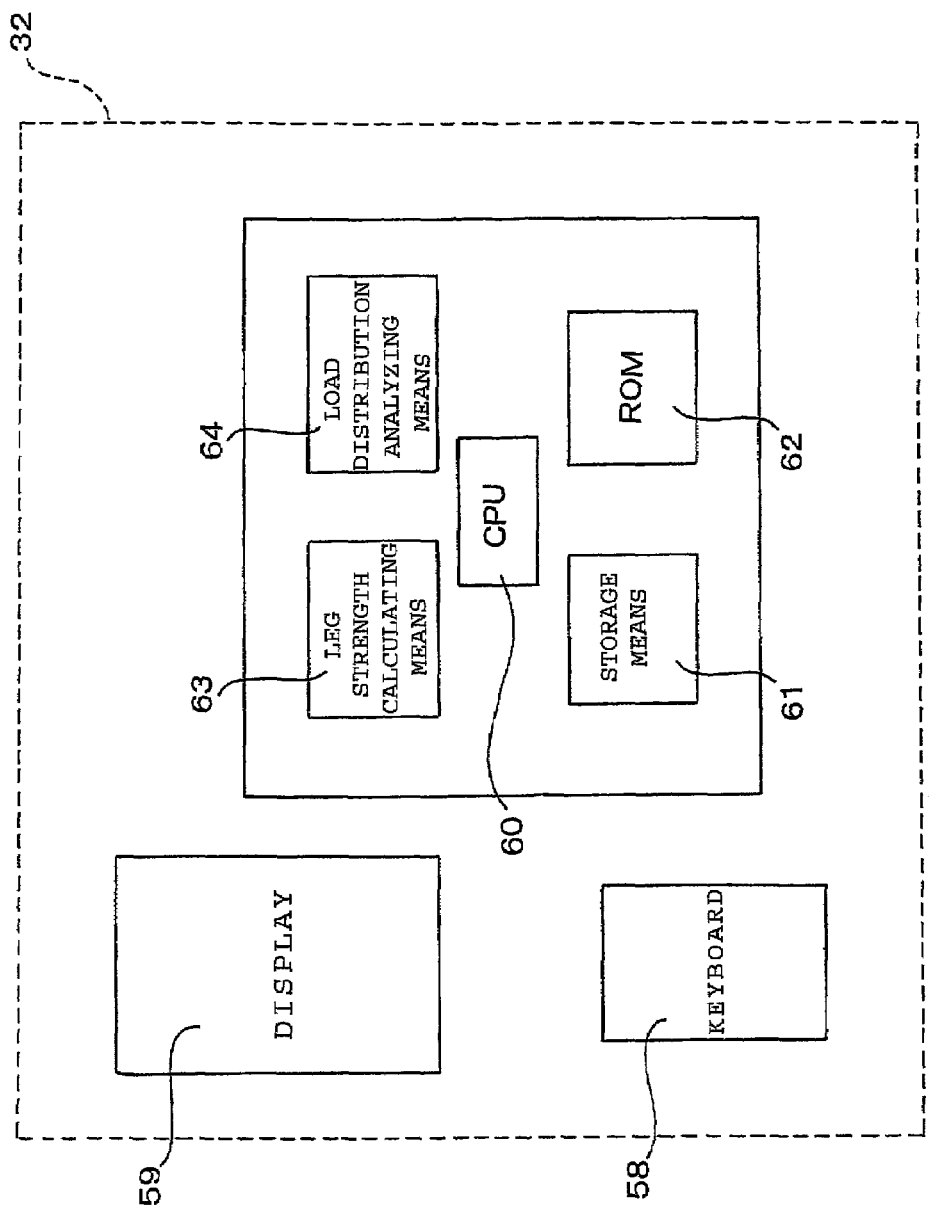
FIG. 12 is a block diagram of a leg strength measuring apparatus.

As shown in FIG. 12, the PC 32 includes a keyboard 58 as an input means, a display 59 as a display means, a CPU 60, RAM as a storage means 61, ROM 62, a leg strength calculating means 63, and a load distribution analyzing means 64.

Figure 13:
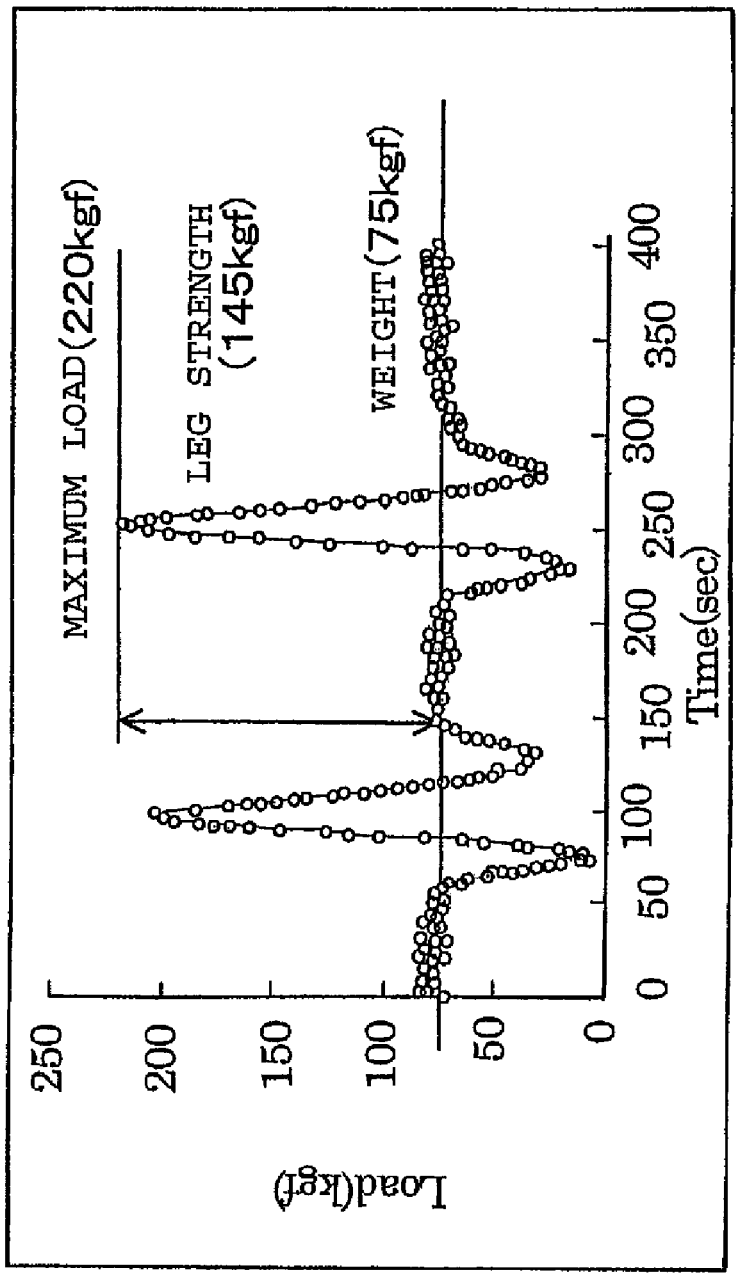
FIG. 13 depicts values measured by the leg strength measuring apparatus.

The storage means 61 stores a series of values measured by the load sensors 36 to 41. That is, when the person has stepped onto the footplates 34 and 35 and made two bending and stretching motions, the values measured in the measurer 31 fluctuate as shown in FIG. 13. The storage means 61 stores a series of these measured values.

The leg strength calculating means 63 calculates the leg strength of the person, as shown in FIG. 13, by subtracting the weight of the person from the maximum load the person applies during his bending and stretching movements. In the case shown in FIG. 13, the maximum load is 220 kgf and the weight is 75 kgf, so that calculated leg strength of the person is 145 kgf, the difference between these two values.

Figure 14:
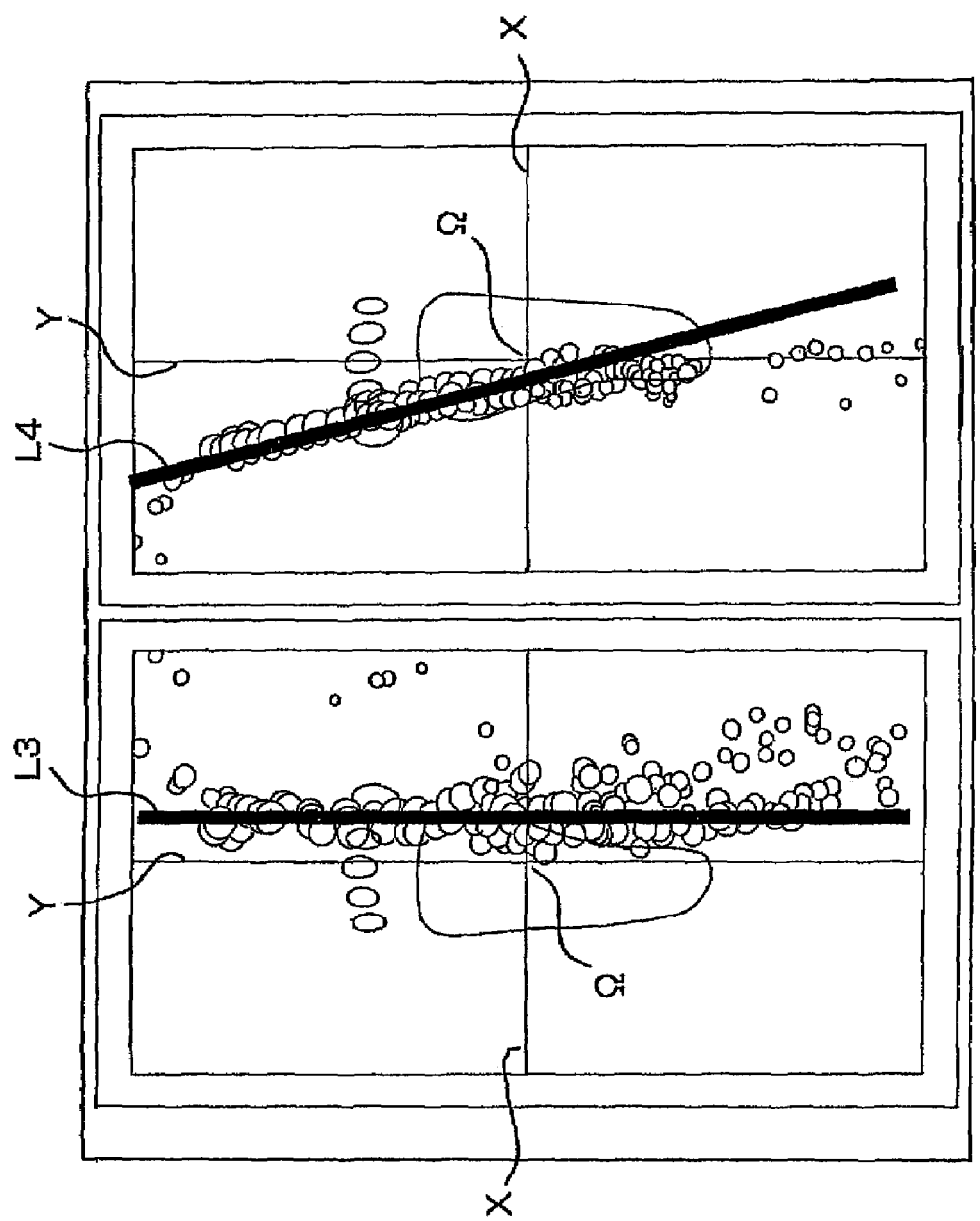
FIG. 14 shows planar distributions of the load values measured by the leg strength measuring apparatus.

The load distribution analyzing means 64 analyzes the state of a gravity center distribution of the loads, based upon the measured values stored in the storage means 61, i.e., the values measured by each of the load sensors 36 to 41. One example of the state of the gravity center distribution of the loads obtained by the load distribution analyzing means 64 is shown in FIG. 14, in which each displayed point indicates the gravity center position of the load at a particular moment. That is, FIG. 14 is a view in which the gravity center positions of the loads are obtained at a pre-determined sampling interval during a pre-determined time and its result is shown by a plurality of points. Next, the method for obtaining the state of the gravity center distribution of the loads will be described. An X-coordinate (XG) of the gravity center of the load at each moment is obtained with a numerical formula 1, and a Y-coordinate (YG) is obtained with a numerical formula 2. A total load F is obtained with a numerical formula 3.

$$XG=(f1-f2)a/F \qquad \text{[Numerical formula 1]}$$

$$YG=(f1+f2-f3)b/F \qquad \text{[Numerical formula 2]}$$

$$F=f1+f2+f3 \qquad \text{[Numerical formula 3]}$$

Figure 11:
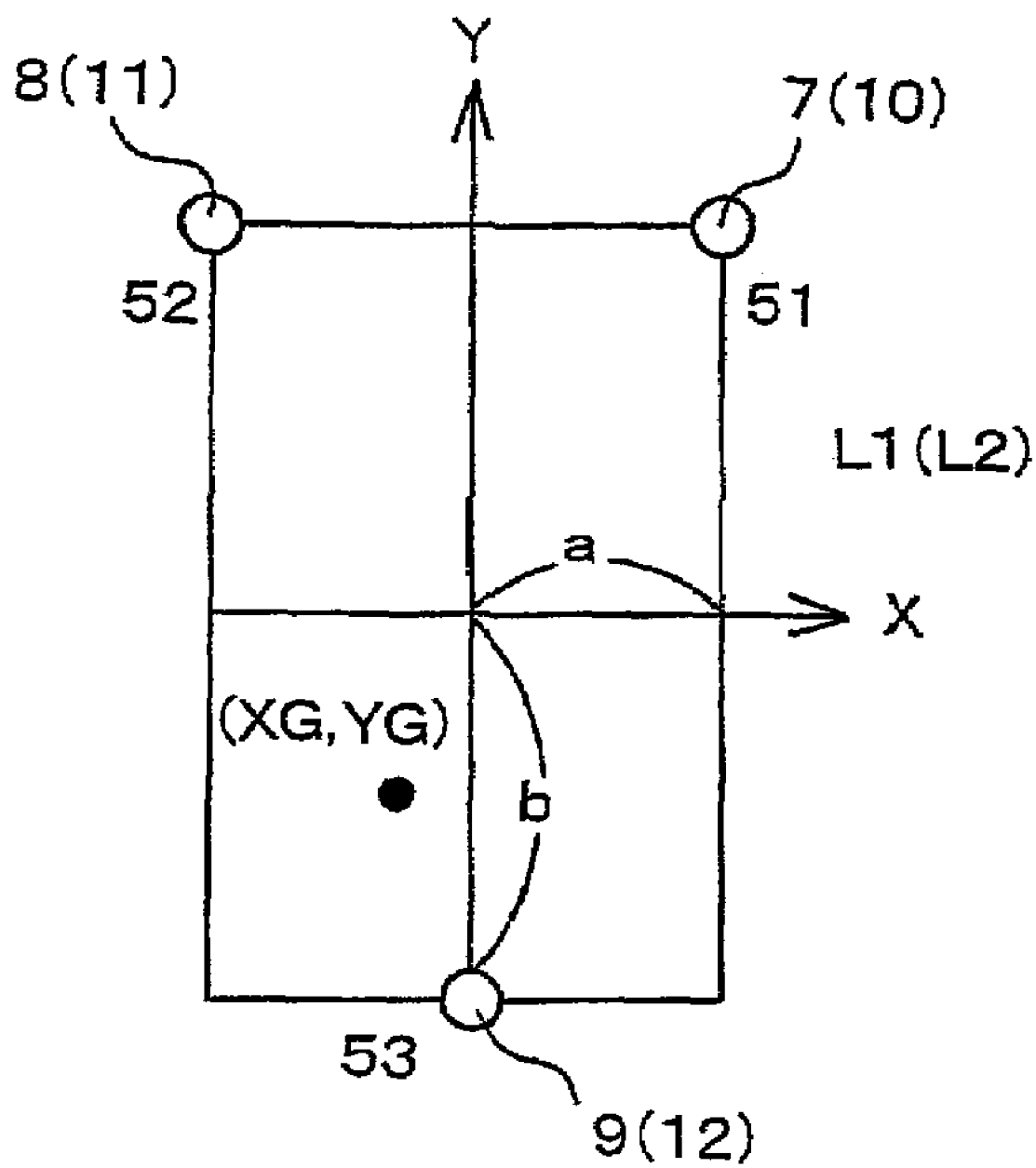
FIG. 11 shows a disposition of load sensors.

As shown in FIG. 11, f1 is the measured value of the load sensor 37 or 40, f2 is the measured value of the load sensor 36 or 39, and f3 is the measured value of the load sensor 38 or 41. In FIG. 14, a Y-axis is set along the axial center L1 of the footplate 34 or the axial center L2 of the footplate 35, and an X-axis is set so that it passes through a center Ω of the footplate 34 or 35 and at right angles to the Y-axis.

Next, a method will be described for making a linear approximation of the changes in the gravity center distribution of the loads that have been determined by the load distribution analyzing means 64 over a period of time. This linear approximation is made using by employing a least-squares method.

The linear approximation is expressed by a numerical formula 4.

$$Y=cX+d \qquad \text{[Numerical formula 4]}$$

In the numerical formula 4, a slope c is obtained by a numerical formula 5.

$$c = \left(\sum_{i=1}^{n} XiYi - n <X><Y>\right) \Big/ \left(\sum_{i=1}^{n} Xi^2 - n<X>^2\right) \qquad \text{[Numerical formula 5]}$$

Here, n indicates the number of data points. In the numerical formula 4, an intersection d is obtained by a numerical formula 6.

$$d=<Y>-c<X> \qquad \text{[Numerical formula 6]}$$

In these formulae, <X> indicates an average coordinate of the X-coordinates over the plurality of the measured load points, and <Y> indicates an average coordinate of the Y-coordinates over the plurality of the measured load points. The intersection d can be obtained with the foregoing numerical formula 6. The best-fit straight lines obtained in such a manner are L3 and L4 in FIG. 14. The leg length calculating means 63 and the load distribution analyzing means 64 can be operated based upon the program software pre-stored in the ROM.

The display means 59 displays the values measured in the load sensors 36 to 41 as a graph, as shown in FIG. 13, in conjunction with an image that displays the distribution of the loads analyzed in the load distribution analyzing means 64, as shown in FIG. 14.

Figure 15:
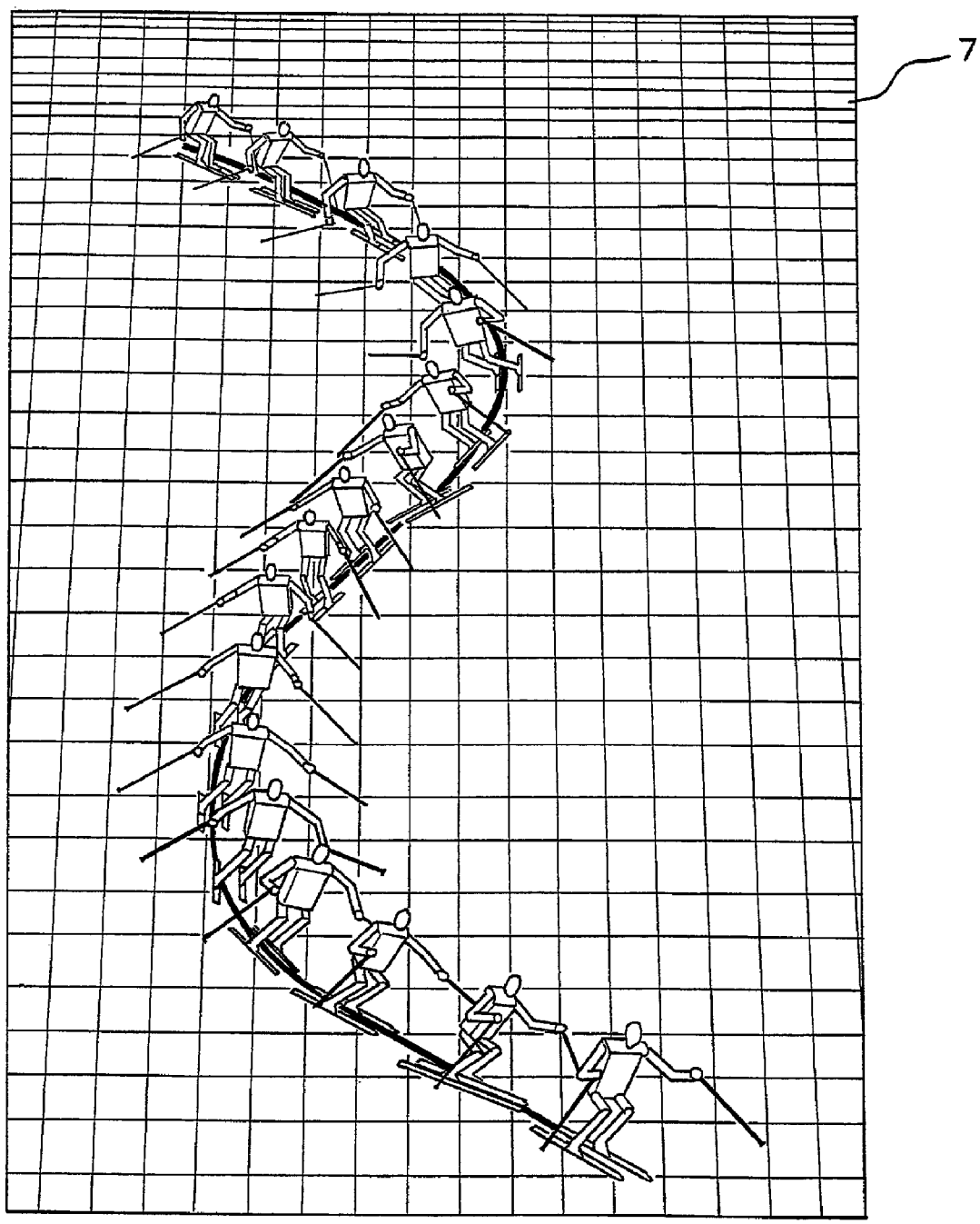
FIG. 15 shows a skiing simulation.
Figure 16:
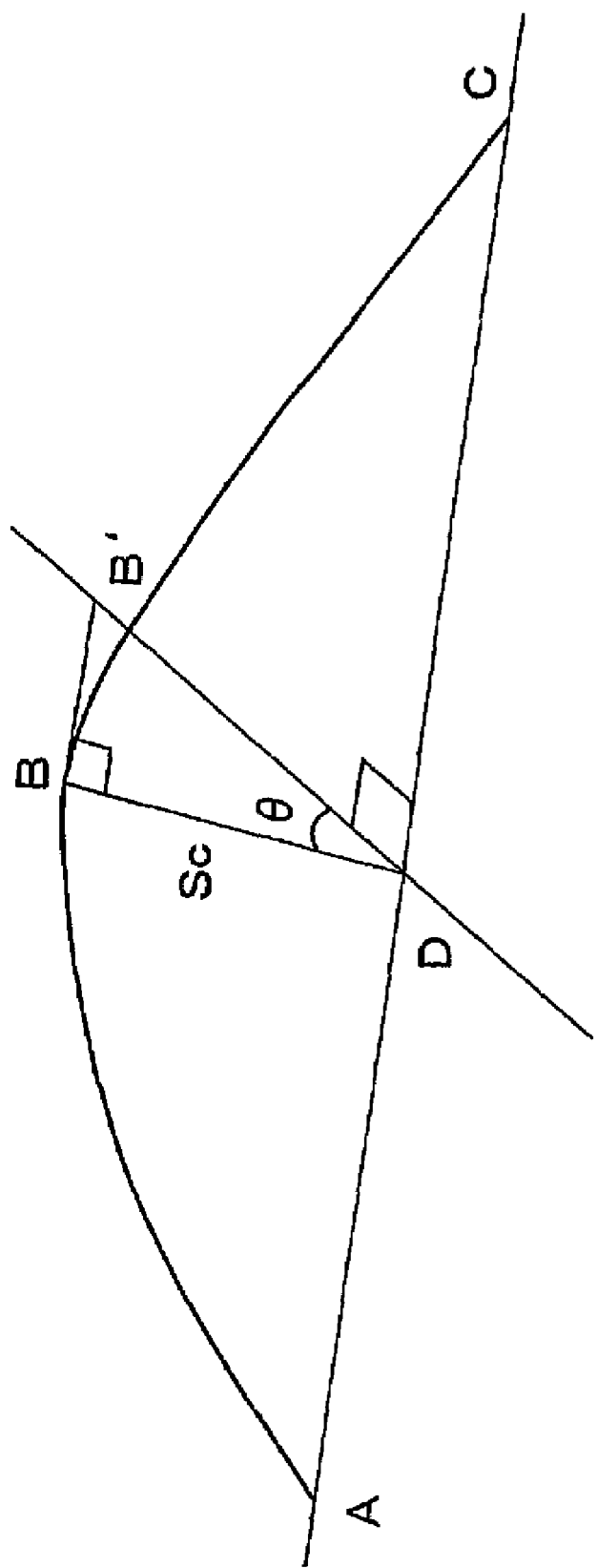
FIG. 16 illustrates a state of edging for a ski.

FIG. 15 shows a simulation of skiing while employing the selected ski or snowboard based upon the weight and leg strength and the skill and technique of the skier or snowboarder as described above. Displaying this simulation requires obtaining a radius of a turn arc, based upon a length, a side curve, etc. of the selected ski or snowboard.

The technique for obtaining a radius of the turn arc of the selected ski or snowboard will be described below based upon FIG. 8, FIG. 9, FIG. 15, and FIG. 16.

As FIG. 9 illustrates, an X-axis is set in the longitudinal direction of the ski, with the Y-axis in the width direction thereof. The tail width (the portion having the widest width in the rear half), the waist width (the portion having a narrow width in the center) and the shoulder width (the portion having a wide width in the front half) of the ski are assumed to be Bh, Bw, and Bs respectively. Furthermore, the distances to these locations from the rear end of the ski are assumed to be Lh, Lw, and Ls respectively. Assuming the points of the tail, the waist and the shoulder on the side curve to be A, B and C, it follows that these coordinates are expressed by A: (Lh, Bh/2); B: (Lw, Bw/2); and C: (Ls, Bs/2), respectively. Furthermore, an intersection point of a straight line AC and a perpendicular from the point B to the straight line AC is assumed to be D, and the distance between B and D to be Sc. Besides, the length CE of a right-angled triangle ACE with a hypotenuse in the straight line AC is assumed to be Z, with ∠CAE (included angle) to be α (alpha).

Figure 17:
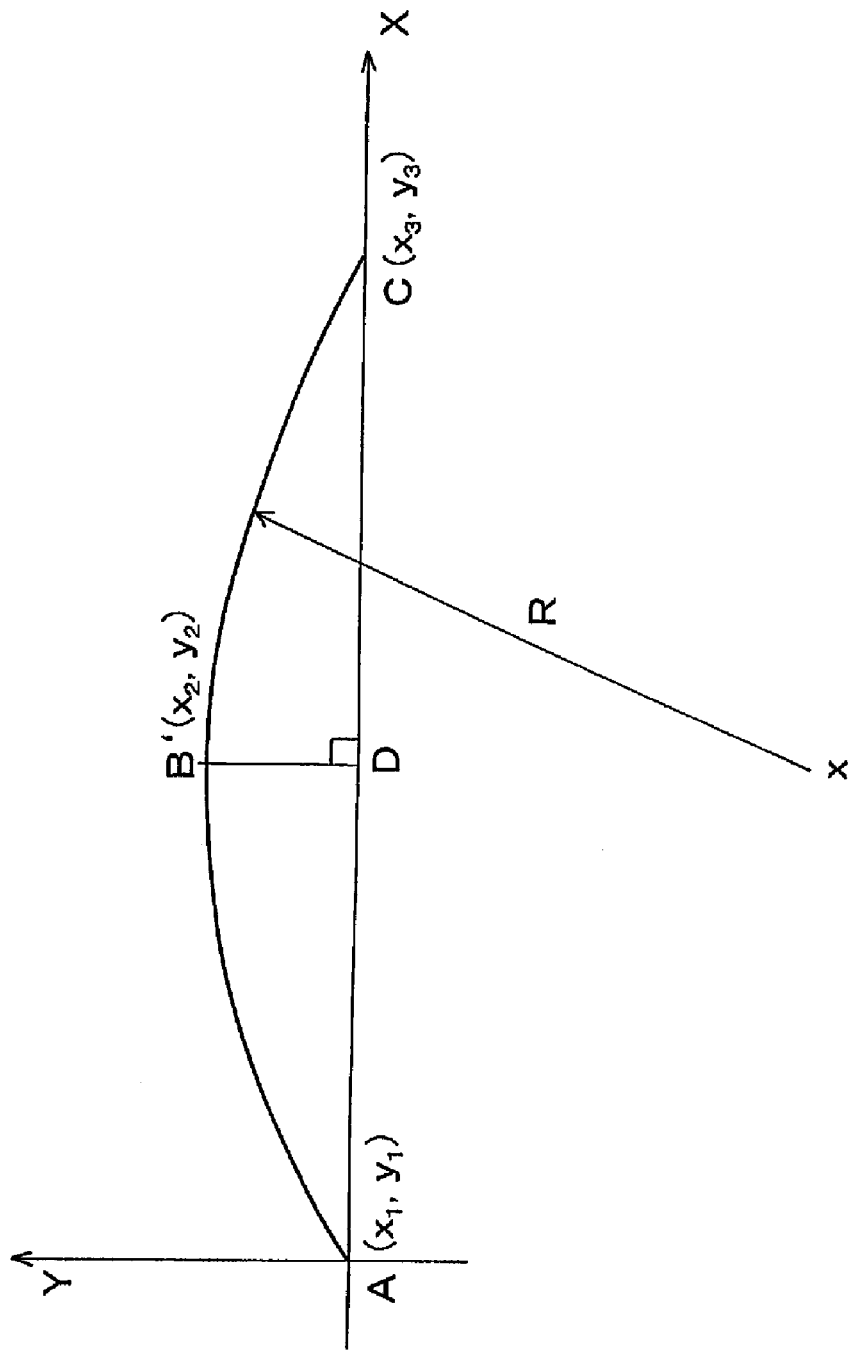
FIG. 17 is a view illustrating a radius of a turn arc while edging with the ski.

Suppose that when edging the ski, the ski rotates about the straight line AC. (See FIGS. 16 and 17, in which the edging angle is assumed to be θ) Next, suppose that the point B is pressed down perpendicularly upon a snow surface in the XY plane. That is, the point B is projected as B'. Suppose that an arc AB'C formed in such a manner is a turn arc corner, and a curvature radius of the circular arc that passes the points A, B' and C is a radius R of the turn arc at while making the edging (where it is supposed that the positions of point A and point B are unchanged.). Under these circumstances, the radius R of the turn arc is obtained in the following manner. First, as shown in FIG. 17, consider the coordinate form with an origin at the point A and with the X-axis in the straight line AC.

Assume the coordinates of the points A, B' and C to be (X1, Y1), (X2, Y2) and (X3, Y3) respectively, then the general numerical formula of the circle that passes through these three points is a numerical formula 7.

$$(X-S)^2+(Y-t)^2=R^2 \qquad \text{[Numerical formula 7]}$$

The center coordinate (S, t) of the circular arc that passes through the three points A, B' and C is obtained by a numerical formula 8.

$$(S,t)=(X_3/2,(X_2^2-X_2X_3+Y_2^2)/2Y_2)) \qquad \text{[Numerical formula 8]}$$

The radius R of the circular arc that passes through the three points A, B' and C is obtained by a numerical formula 9.

$$R=\sqrt{(X_3/2)^2+[(X_2^2-X_2X_3+Y_2^2)/(2Y_2)]^2} \qquad \text{[Numerical formula 9]}$$

Furthermore, assuming the number of turns made when the skier travels a distance of 100 m in the X direction to be T, then the radius R can be obtained by T=100/2R.

Figure 18:
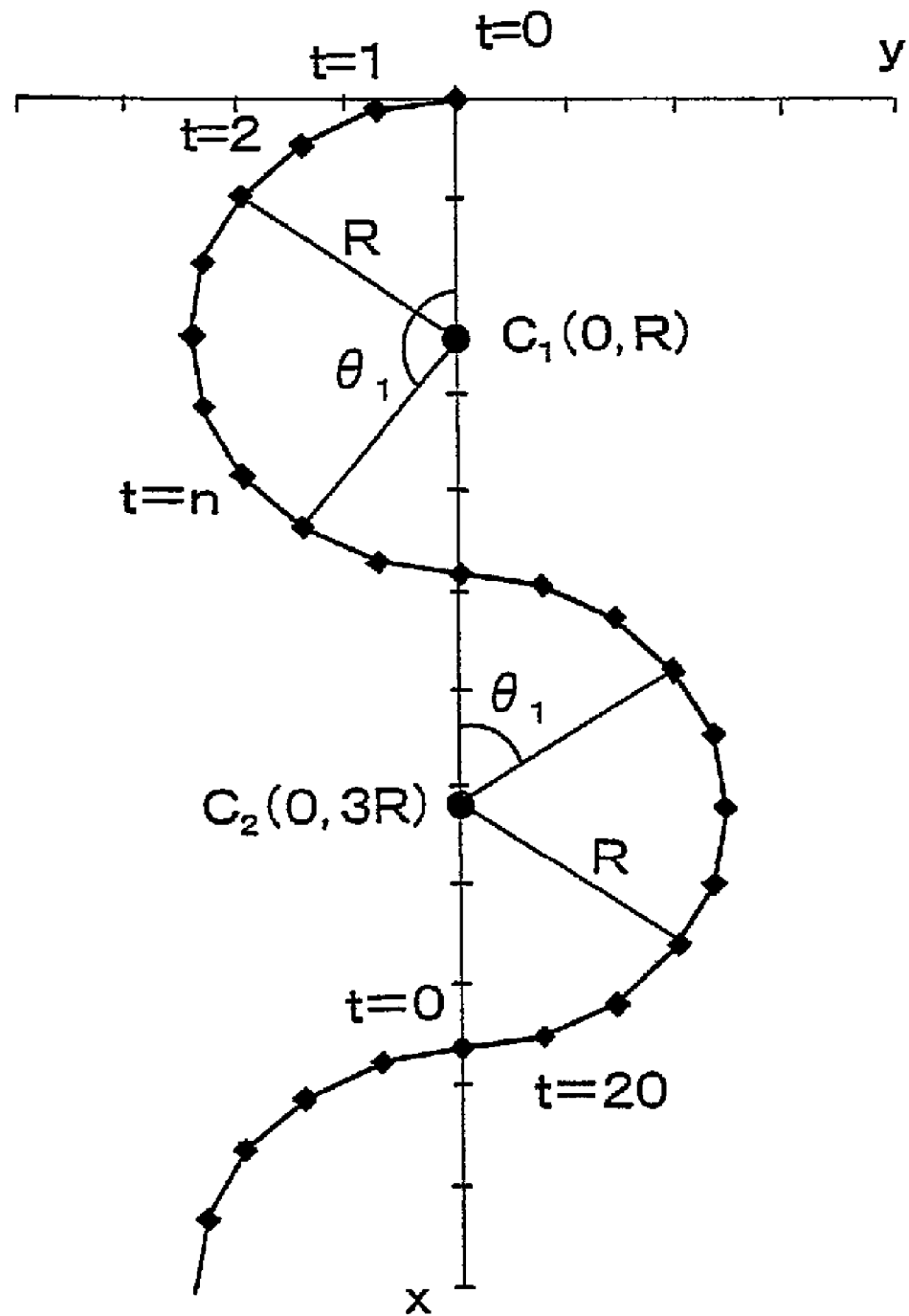
FIG. 18 is a view illustrating a point-by-point display of a turn.
Figure 19:
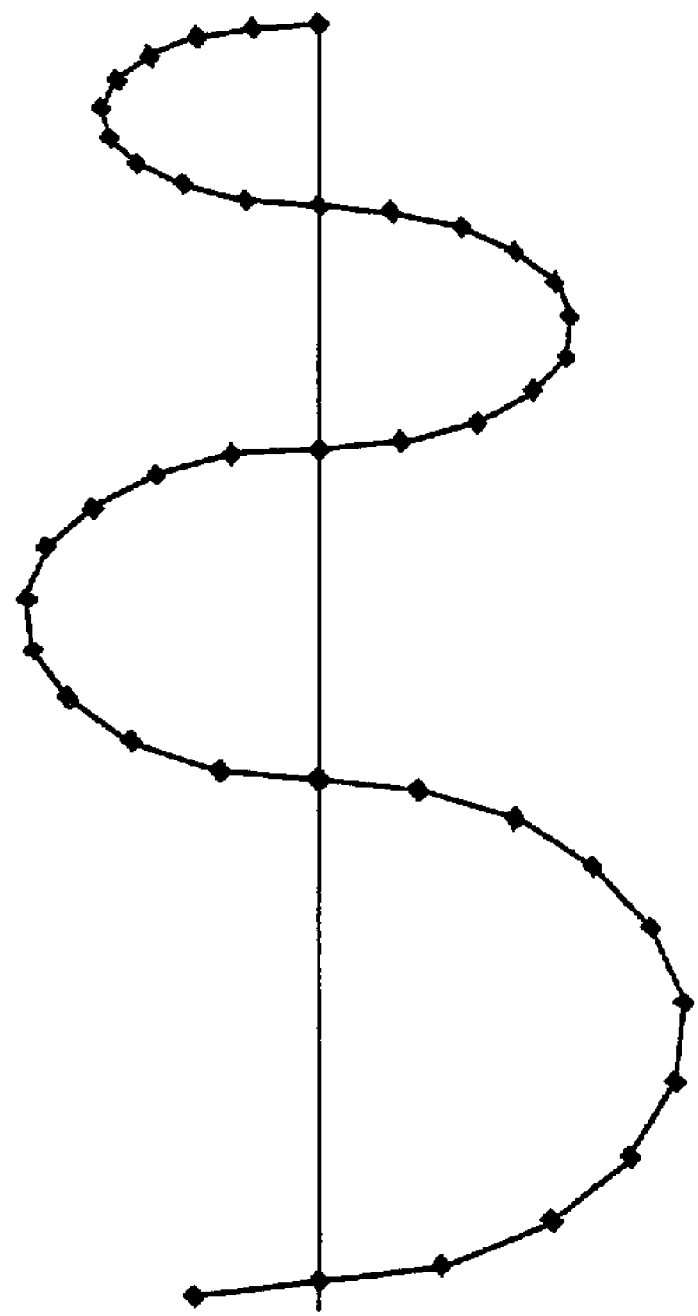
FIG. 19 is a view illustrating a state obtained by coordinate-converting the information in FIG. 18 into a view taken obliquely from the front.

When displaying a turn locus, as shown in FIG. 18, an XY coordinate form system is employed. The ski turn that transitions from a left turn to a right turn can be displayed by the following general numerical formula with the edging angle, the widths of the three principal points of the ski, and the radius R of the turn arc calculated from their positions. When a numerical value K that decides a direction of the ski is odd, it indicates the left turn, and when the numerical value R is even, it indicates the right turn.

K=1, 3, 5, 7, . . .

$$X=[2(K-1)-\cos\theta_t]R$$

$$Y=-R\sin\theta_t$$

K=2, 4, 6, 8, . . .

$$X = [(2K-1) - \cos\theta_t]R$$

$$Y = R \sin\theta_t \qquad \text{[Numerical formulae 10]}$$

As shown in FIG. 18, displaying the foregoing X and Y coordinates as a series of displayed points displays a stationary image of a series of ski or snowboard turns.

Figure 20:
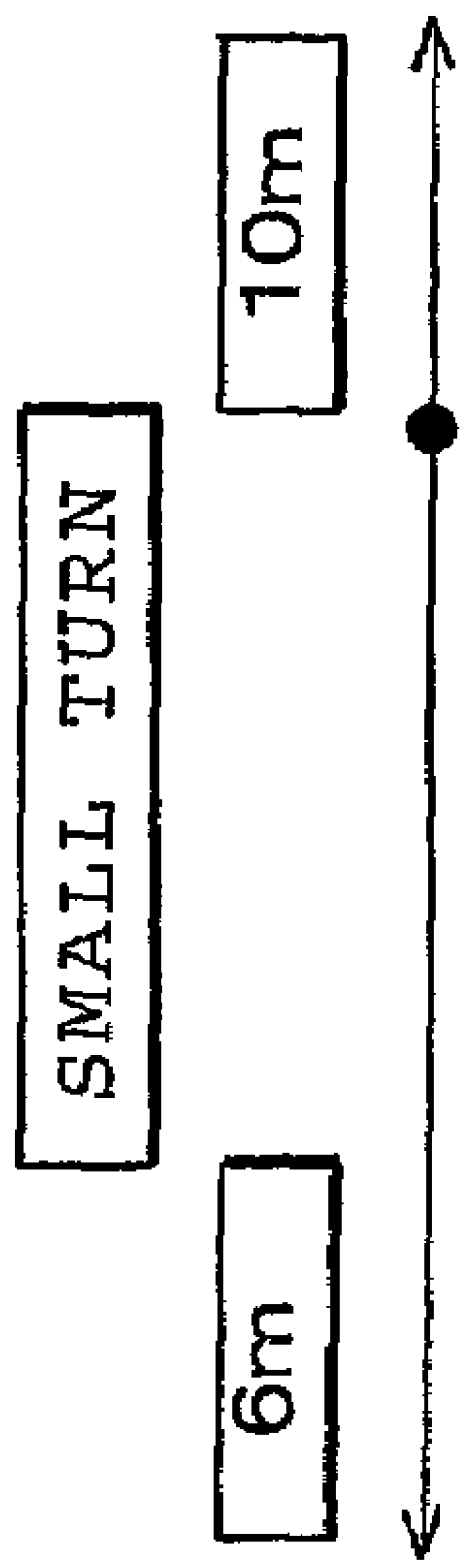
FIG. 20 is a view illustrating a relation between the radius of the turn arc of a small turn technique selected by the skier or snowboarder and the determined radius of a turn arc of a ski or snowboard determined to be appropriate.
Figure 21:
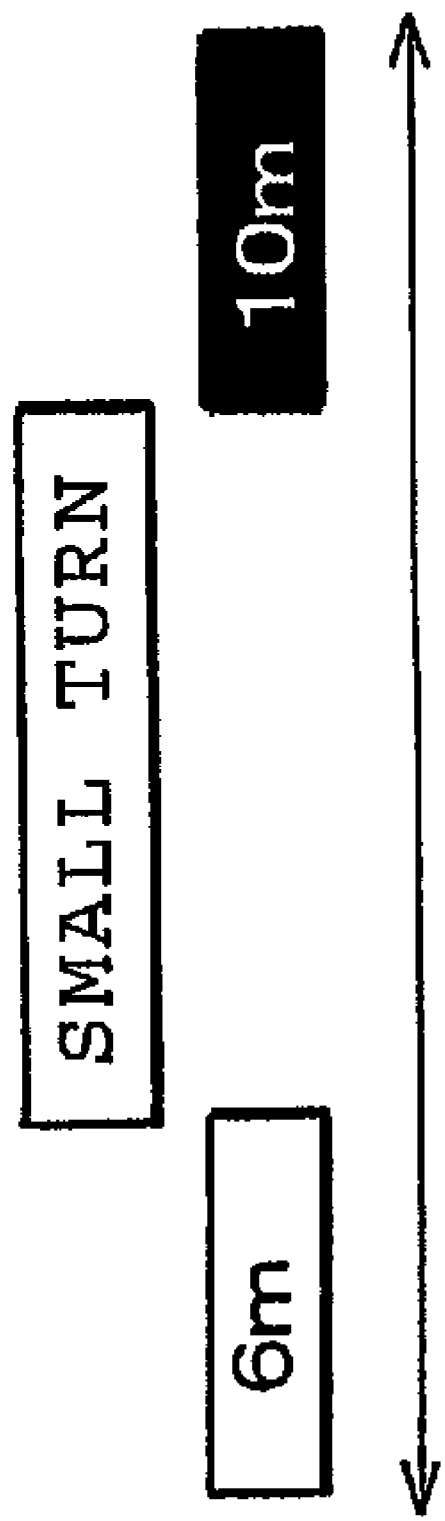
FIG. 21 is a view similar to that of FIG. 20, but one that illustrates a situation in which the ski or snowboard may not be appropriate.

Additionally, as shown in FIG. 6, a classification of a large turn, a middle turn, or a small turn may be input, depending upon the individual taste of the skier or snowboarder. When a ski or snowboard judged to be suitable for each skier or snowboarder is suitable for a large turn, a middle turn, or a small turn, as selected by taste of each skier or snowboarder, its effect may be displayed. When, on the other hand, it is not suitable, its effect may also be displayed accordingly. For example, FIG. 20 displays a situation in which the radius of the turn arc of the ski or snowboard judged to be suitable for an individual skier or snowboarder is included in a range of small turns and is thus suitable for a small turn as shown by a point in FIG. 20. On the other hand, in FIG. 21, the fact that the radius of the turn arc of the ski or snowboard judged to be suitable for the individual skier or snowboarder is not included in the range of small turns is displayed by displaying an upper limit of the range of the small turns as a black box, thereby communicating that the radius exceeds the upper limit displayed.

In the embodiment described above, the PC 32 for obtaining the weight, leg strength, and maximum load of the skier or snowboarder, and the PC 3 that includes the board characteristic determining means and the board searching means are separately provided; however a single PC may be arranged so as to serve the functions of both of these two PCs.

In the above embodiment, the ski or snowboard suitable for the weight, leg strength, and the skill or technique of the skier or snowboarder is judged; the ski or snowboard suitable for each skier or snowboarder may also be judged based on other factors such as, for example, the technique that suits the taste of the skier or snowboarder, the user's height, body type, or age.

Providing a fixation section for fixing the ski or snowboard boots onto the footplates 34 and 35 and measuring the load in a state where the person is wearing the ski or snowboard boots enables the leg strength, etc. to be measured in a situation closer to that of actual use. Furthermore, the person may stand and move on the footplates 34 and 35 to measure the load while wearing ski or snowboard boots along with the skis or the snowboard.

The footplates 34 and 35 may be provided horizontally, but placing the footplates 34 and 35 in a position that is inclined from front-to-back or left-and-right with respect to the axial centers L1 and L2 of the footplates 34 and 35 makes it possible to measure the leg strength of the person and the gravity center distribution in a state more like actual skiing or snowboarding. This can include conditions in which the toes are raised or lowered or the feet are swung left and right while the person is standing and moving on the footplates 5 and 6.

What is claimed is:

1. A system for assisting a user in the selection of a ski or snowboard, the system comprising:

a data storage device configured to store data corresponding to bend characteristics of a plurality of skis or snowboards;

leg strength measurement apparatus comprising:
   at least one footplate configured to receive and support a person for whom a ski or snowboard is to be selected; and
   a load sensor operable to detect loads applied to the footplate, and;
   leg strength calculation apparatus operable to calculate the person's leg strength based at least in part on a subtraction of a value corresponding to a load detected while the person is standing stationary on said at least one footplate from a value corresponding to a maximum load detected while the person is making bending and stretching movements on said at least one footplate;

a board characteristic selection device operable to determine an appropriate bend characteristic of a ski or snowboard based at least in part on the person's leg strength as calculated by the leg strength calculation apparatus;

a board selection device operable to select a ski or snowboard corresponding to the appropriate bend characteristic determined by the board characteristic selection device based on the data stored in the data storage element; and a communication device operable to communicate the identity of the ski or snowboard selected by the board selection device to the user.

2. The system of claim 1, wherein said at least one footplate comprises two footplates, each said footplate being configured to receive and support each one of two feet of the person for whom the ski or snowboard is to be selected.

3. The system of claim 2, wherein the load sensor is operable to detect loads applied to each footplate at three or more points.

4. The system of claim 2, wherein the load sensor is operable to detect a vertical load applied to each footplate, and a moment associated with that vertical load.

5. The system of claim 1, and further comprising structure configured to receive and fix in place on the footplate a boot to be worn by the person for whom the ski or snowboard is to be selected, while that person is standing on the footplate.

6. The system of claim 1, and further comprising structure configured to receive and fix in place on the footplate an item selected from the group consisting of a ski and a snowboard, while the person whose leg strength is to be measured is standing on the item on the footplate.

7. The system of claim 1, and further comprising structure operable to fix the footplate in a position inclined in at least one of a front-to-back and a transverse direction.

8. The system of claim 1, wherein the communication device includes a video display screen operable to identify the ski or snowboard selected by the board selection device to the user.

* * * * *